United States Patent [19]

Chang et al.

[11] Patent Number: 4,540,709

[45] Date of Patent: Sep. 10, 1985

[54] METHOD FOR TREATMENT OF DISEASES MEDIATED BY PAF USING 5-ALLYL-2-(3,4-DIMETHOXYPHENYL)-3A,α-METHOXY-3-METHYL-2,3,3A,6-TETRAHYDRO-6-OXOBENZOFURAN

[75] Inventors: Michael N. Chang, Westfield; San-Bao Hwang, Scotch Plains, both of N.J.

[73] Assignee: Merck & Co., Inc., Rahway, N.J.

[21] Appl. No.: 541,806

[22] Filed: Oct. 13, 1983

[51] Int. Cl.$^3$ .............................................. A61K 31/34
[52] U.S. Cl. .................................... 514/470; 549/466
[58] Field of Search ......................... 549/466; 424/285

[56] References Cited

PUBLICATIONS

Iida et al., I, Phytochemistry, Dec. 1982, 21(12), pp. 2939–2941.

Iida et al., II, Phytochemistry, Mar. 1982, 22(3), pp. 763–766.
K. Matsui et al., Agr. Biol. Chem., 40, 1045 (1976).
K. Matsui et al., Agr. Biol. Chem., 40, 1113 (1976).

*Primary Examiner*—Henry R. Jiles
*Assistant Examiner*—Bernard I. Dentz
*Attorney, Agent, or Firm*—Theresa Y. Cheng; Mario A. Monaco

[57] ABSTRACT 5-allyl-2-(3,4-dimethoxyphenyl)-3a,α-methoxy-3-methyl-2,3,3a,6-tetrahydro-6-oxobenzofuran and analogs thereof as PAF-antagonists have been isolated from *Piper futokadsura Sieb, et Zucc.* and its analogs prepared. These neolignan compounds are found to have potent and specific PAF (Platelet-Activating-Factor) antagonistic activities and are thereby useful in the treatment of various diseases or disorders mediated by the PAF, for example, inflammation, cardiovascular disorder, asthma, lung edema, and adult respiratory distress syndrome.

1 Claim, 1 Drawing Figure

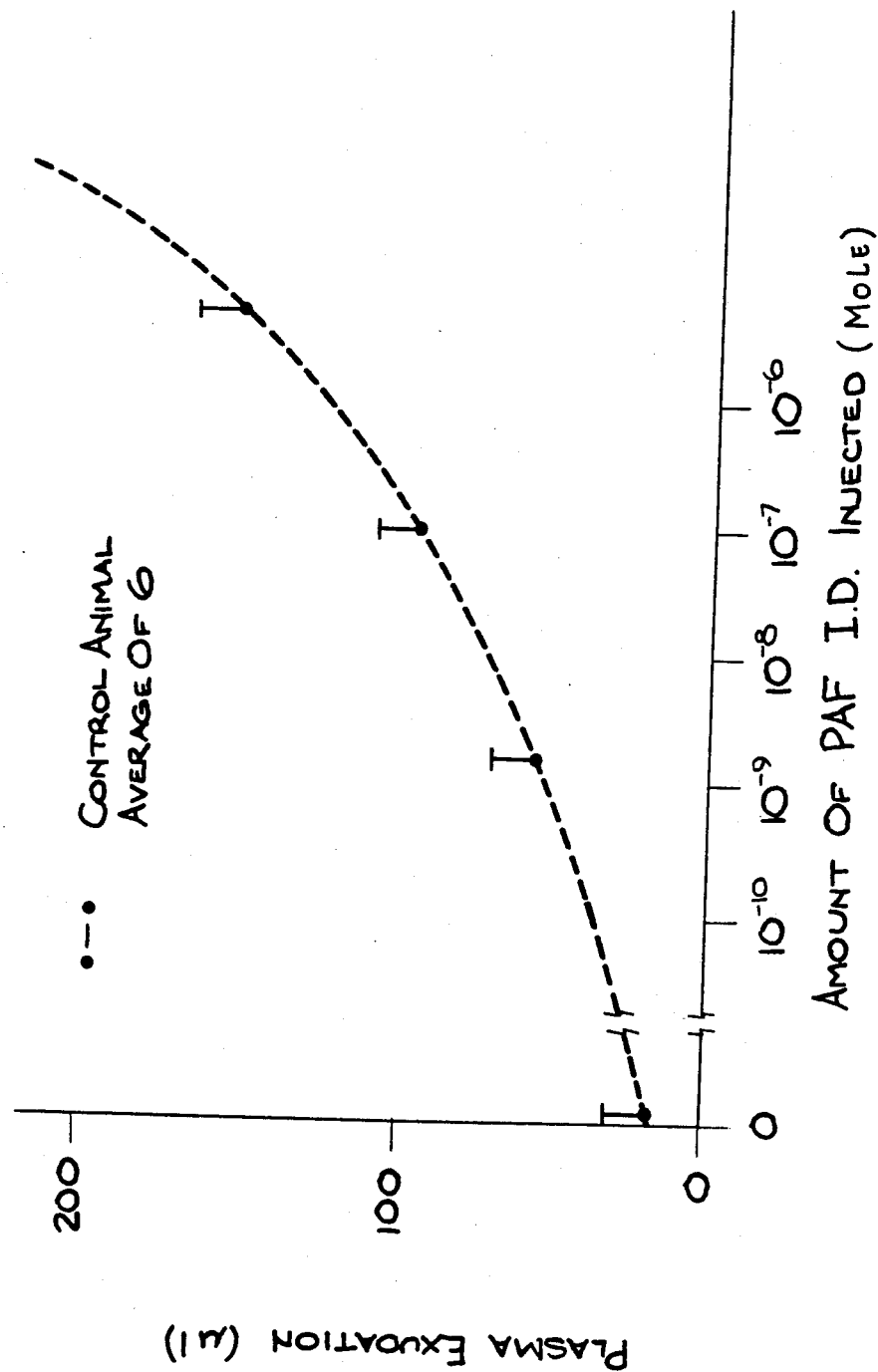

METHOD FOR TREATMENT OF DISEASES MEDIATED BY PAF USING 5-ALLYL-2-(3,4-DIMETHOXYPHENYL)-3A,α-METHOXY-3-METHYL-2,3,3A,6-TETRAHYDRO-6-OXOBENZOFURAN

BACKGROUND OF THE INVENTION

Platelet-activating factor (PAF) has recently been identified as an acetyl glyceryl ether phosphorylcholine (AGEPC), i.e., 1O-hexadecyl/octadecyl-2-O-acetyl-sn-glyceryl-3-phosphorylcholine (Hanahan, D. S. et al., *J. Biol. Chem.*, 255:5514, 1980). Even before its chemical identification, PAF has been linked to various biologic activities and pathways making it one of the important mediators responsible for a variety of physiological processes including activation or coagulation of platelets, pathogenesis of immune complex deposition, smooth muscle contraction, inflammation as well as respiratory, cardiovascular and intravascular alterations. These physiological processes are known to be associated with a large group of diseases, for example, inflammatory diseases, cardiovascular disorders, asthma, lung edema, and adult respiratory distress syndrome. It is therefore only natural that more and more scientific investigators are focusing their work on the search of a PAF-antagonist or inhibitor for the treatment and/or the prevention of these common diseases.

The novel compound of the present invention, 5-allyl-2-(3,4-dimethoxyphenyl)-3a,α-methoxy-3-methyl-2,3,3a,6-tetrahydro-6-oxobenzofuran (I), is a potent and specific PAF-antagonist isolated from the Chinese herbal plant Piper futokadsura Sieb. et Zucc.

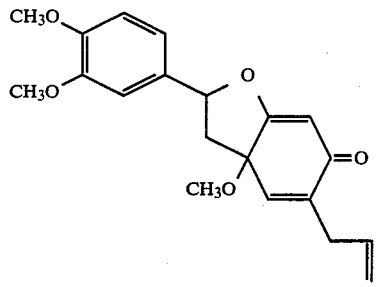

Although the plant Piper futokadsura Sieb. et Zucc. itself has been used by the Chinese as an herb medicine for the treatment of arthritis conditions, we have for the first time isolated compound (I) from this herb and discovered its property as a specific PAF-antagonist useful not only for the treatment of arthritic conditions but also for other diseases including asthma, hypertension, lung-edema, adult distress syndrome and the like.

Accordingly, it is the object of the present invention to provide compound (I) as a specific PAF-antagonist.

Another object of this invention is to provide processes for the isolation of compound (I).

A further object of this invention is to provide a pharmaceutically acceptable composition containing compound (I) as the active ingredient for the treatment of diseases which are subject to the mediation of a PAF-antagonist.

Still a further object of this invention is to provide a method of treatment comprising the administration of a therapeutically sufficient amount of compound (I) to a patient suffering from various skeletal-muscular disorders including but not limited to inflammation, e.g., osteoarthritis, rheumatoid arthritis and gout; hypertension; cardiovascular disorder; asthma; lung edema; or adult respiratory distress syndrome.

DETAILED DESCRIPTION OF THE INVENTION

A. Scope of the Invention

This invention relates to the specific PAF-antagonist 5-allyl-2-(3,4-dimethoxyphenyl)-3a,α-methoxy-3-methyl-2,3,3a,6-tetrahydro-6-oxobenzofuran.

B. Isolation of Compound (I)

Compound (I) was isolated from Piper futokadsura Sieb using the following method:

A crude methylene chloride extract of the plant (200 mg) in 0.5 ml methylene chloride was chromatographed under moderate pressure (5–6 psi) on a flush column, for example, a silica column of 1 inch in diameter and packed with 50 g of silica (Kieselgel 60, 200–400 mesh). After the column was equilibrated with 10% ethyl acetate in hexane, it was eluted with a solvent gradient system involving 10–20% mixtures of ethyl acetate in n-hexane; ethyl acetate; and methanol. The fraction having biological activity was concentrated to obtain the purified compound (I).

MS: m/e: 356.19 (M+), 178 (100%)

IR: $_{max}$(CH$_2$Cl$_2$): 1671, 1629, 1520 cm$^{-1}$

NMR (CDCl$_3$): δ1.35 (3H, d, J=7.5Hz), 2.87 (1H, q, J=6.1 Hz), 3.23 (3H, s), 3.33 (2H, d, J=7.0 Hz), 4.09 (3H, s), 4.11 (3H, s), 5.2–5.4 (2H, m), 6.05 (1H, s), 6.35 (1H, s), 7.1 (2H, broad s), 7.2 (1H, broad s).

C. Utility of the compounds within the scope of the invention

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active constituent.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by the PAF, compound (I) may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or koalin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 25 to about 75 mg of the compound per kilogram of body weight per day (about 75 mg to about 3.75 gms per patient per day). Advantageously, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

It has been found that the compound (I) exhibits in vitro and in vivo antagonistic activities with respect to the PAF:

A. In Vitro Assay

In vitro, compound (I) inhibits PAF-induced functions in both the cellular and the tissue levels by disturbing the PAF binding to its specific receptor site. The ability of compound (I) to inhibit the PAF binding to its specific receptor binding site on rabbit platelet plasma membranes was measured by an assay recently developed by us.

The inhibition of $H^3$-PAF binding to the rabbit platelet plasma membrane by compound (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of compound (I) as the antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 μg of the platelet plasma membrane suspension (S. B. Hwang, et al., *Biochemistry*, in press) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0° C.) Tris-buffer solution. Ten millimeters of scintillation solution (Aquasol 2, New England Nuclear, Connecticut) was added with stirring to each filter containing the washed residue, and the radioactivity of each resulting suspension was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equation:

$$\% \text{ Inhibition} = \frac{(\text{Total binding } C_1) - \text{Total binding with antagonist}}{\text{Specific binding}} \times 100$$

$$\frac{\text{Specific}}{\text{binding}} = (\text{Total binding } C_1) - (\text{non-specific binding } C_2)$$

From our observation, compound (I) inhibits in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle contraction. It is also shown that they are highly specific to PAF. For example, they do not inhibit the binding of $H_1$ antagonist ($^3$H-pyrilamine) to guinea pig brain membrane, nor do they inhibit the cholecystokinin (CCK) binding to its receptor based on an assay on isolated rat pancreas membrane. Furthermore, they affect no or only minute inhibition on the histamine-induced ileum contraction in guinea pigs.

The in vitro activity of compound (I) was determined by the assay to have an $IC_{50}$ value of $1.74 \times 10^{-7}$M.

B. In Vivo Assay

The specific PAF-antagonistic activities are further established by an in vivo assay (modified procedure of Humphrey et al., *Lab. Investigation* 46, 422 (1982)) following the protocol described below:

Protocol for the evaluation of the oral activity of PAF antagonists or the inhibition of PAF-induced increase of vasopermeability by PAF-antagonists I. Animal species: 5 guinea pigs (400–500 g)
II. Material:
  0.5% (w/v) aqueous methylcellulose solution sodium nembutol
  2% Evans Blue solution: 2 g of Evans Blue in 100 ml of pH 7.5 Tris-buffer solution
  Tris-Buffer solution: 150 mM NaCl and 10 mM Tris in 1 ml of water with pH adjusted to 7.5.
III. Procedure
  1. Weigh the guinea pigs. Label them as control, $T_1$, $T_2$, $T_3$ and $T_4$.
  2. Fast the animals overnight.
  3. Weigh the animals again after the fasting.
  4. Ground and suspend a PAF antagonist such as compound (I) with intensive sonication in 3 ml of 0.5% aqueous methylcellulose solution.
  5. Administer orally to each of the animals $T_1$, $T_2$, $T_3$ and $T_4$ an appropriate amount (in terms of mg/kg of bodyweight) of the antagonist solution from 4.), except the control animal which should receive only the 0.5% aq. methylcellulose solution.
  6. Forty minutes after the oral administration, anesthetize the animals with sodium nembutol (0.75 ml/kg i.p.).
  7. After 20 minutes or when tne anesthetics became effective, inject intracardially to each animal 2 ml/kg body weight of the 2% Evans Blue solution.
  8. Wait for 10 minutes. In the meantime, shave the backs of the guniea pigs and get ready for the PAF injection. Select two rows of 5 (a total of ten) sites on the back of each animal and designate them as sites

| 1a | 2a | 3a | 4a | 5a |
|----|----|----|----|----|
| 1b | 2b | 3b | 4b | 5b | and inject intracutaneously, in duplicate 0.1 ml of a PAF solution in Tris-buffer or 0.1 ml of the Tris-buffer itself (control) according to the following schedule:

| Sites | Solution to be injected |
|---|---|
| 1a | Tris-buffer |
| 1b | " |
| 2a | $5 \times 10^{-9}$ g/ml PAF |
| 2b | " |
| 3a | $5 \times 10^{-8}$ g/ml PAF |
| 3b | " |
| 4a | $5 \times 10^{-7}$ g/ml PAF |
| 4b | " |
| 5a | $5 \times 10^{-6}$ g/ml PAF |
| 5b | " |

Repeat the same injection on the backs of the remaining animals.

9. Wait for 30 minutes or until the blue color developed into a steady shade on each injection site. Open the chest of each animal, extract by cardiac puncture 1 ml of blood and transfer it to a marked centrifuge tube. Centrifuge all the blood samples at about 2000×g for 10 minutes and decant the blue tinted supernatants (plasma). Set aside these plasma samples for later spectroscopic measurements.

10. Sacrifice the animals and remove the back skin of each of them. Isolate with a 20 mm diameter steel punch the injection sites (blue spots) into individual discs of skin and dissect each of the skin discs into about 10–20 pieces.

11. Mix in a 50 ml polyethylene test tube the skin pieces from a particular injection site with a medium containing 14 ml of acetone and 6 ml of 0.5% aqueous solution of sodium sulfate. See Harada, M., et al., *J. Pharm. Pharmacol.* 23, 218–219 (1971) for detailed procedures. Repeat the same procedures for each individual injection site.

12. Homogenize the contents of each test tube on a polytron (Kinematica GmbH, Switzerland) with setting at 5 for 10–20 seconds.

13. In the meantime, extract a 100 μl sample of each of the plasma set aside in Step (9) with the same acetone-aqueous sodium sulfate solution used in Step (11). Set aside the resulting extracts for later determination of the Evans blue concentration in the plasma of each animal.

14. Centrifuge the skin preparations from Step (12) for 10 minutes at 750 ×g and decant the supernatants for the following spectroscopic determination.

15. Measure the absorbance of each supernatant from Step (14) ("skin sample") as well as the plasma extract from Step (13) ("plasma sample") at 620 nm with a Cary 210 spectrophotometer (Varian, Palo Alto, Calif.). Calculate the amount of Evans blue in each skin sample in terms of the volume (μl) of the exuded blood plasma according to the following equation:

$$\text{Exuded plasma at a particular injection site (μl)} = \frac{\text{Absorbance (at 620 nm) of "skin sample"}}{\text{Absorbance (at 620 nm) of "plasma sample" of the same animal}} \times 100 \quad \text{(II)}$$

16. Draw a plasma exudation curve.

17. Calculate the percent inhibition of PAF-induced cutaneous vascular permeability from measuring the area under the plasma exudation curve of the control animal ($A_C$) and those of the animals treated orally with an antagonist ($A_D$) according to the following equation % inhibition observed from the guinea pig $T_1$ treated with $x$ mg/kg of antagonist $X$.
= % inhibition at $x$ mg/kg dosage level of antagonist $X$.

$$= \frac{A_C - A_D}{A_C} \times 100\%$$

$$= \left(1 - \frac{A_D}{A_C}\right) \times 100\%$$

where the ratio $A_D/A_C$ can be determined from the weight of the paper under the plasma exudation curve of the control curve ($A_C$) and that under the plasma exudation curve of the treated animal $T_1(A_D)$.

The following table summarizes the in vivo results:

TABLE I

| % Inhibition of PAF Receptor by Compound (I) | |
|---|---|
| Dose (mg/kg P.O.) | % inhibition |
| 50 | 63 |
| 25 | 43 |

$ED_{50}$ = 30 mg/kg P.O.

What is claimed is:

1. A method of treatment of diseases or conditions mediated by platelet-activating factor comprising the administration to a mammalian species in need of such treatment a therapeutically effective amount of substantially pure 5-allyl-2-(3,4-dimethoxyphenyl)-3a,α-methoxy-3-methyl-2,3,3a,6-tetrahydro-6-oxobenzofuran.

* * * * *